(12) United States Patent  
Voudouris

(10) Patent No.: US 9,585,733 B2  
(45) Date of Patent: Mar. 7, 2017

(54) ORTHODONTIC BRACKET WITH ANGLED, CURVED SHUTTER

(71) Applicant: Orthoarm, Inc., Toronto (CA)

(72) Inventor: John Voudouris, Toronto (CA)

(73) Assignee: Orthoarm, Inc., Toronto, Ontario (CA)

( * ) Notice: Subject to any disclaimer, the term of this patent is extended or adjusted under 35 U.S.C. 154(b) by 288 days.

(21) Appl. No.: 14/171,911

(22) Filed: Feb. 4, 2014

(65) Prior Publication Data

US 2015/0216629 A1    Aug. 6, 2015

Related U.S. Application Data

(63) Continuation-in-part of application No. 13/852,351, filed on Mar. 28, 2013, now Pat. No. 9,339,353.

(60) Provisional application No. 61/616,462, filed on Mar. 28, 2012.

(51) Int. Cl.
*A61C 7/30* (2006.01)
*A61C 7/28* (2006.01)

(52) U.S. Cl.
CPC .............. *A61C 7/287* (2013.01); *A61C 7/30* (2013.01)

(58) Field of Classification Search
CPC .............. A61C 7/287; A61C 7/30; A61C 7/20
See application file for complete search history.

(56) References Cited

U.S. PATENT DOCUMENTS

| | | | |
|---|---|---|---|
| 4,712,999 A | 12/1987 | Rosenberg |
| 5,474,445 A | 12/1995 | Voudouris |
| 5,630,715 A | 5/1997 | Voudouris |
| 5,857,850 A | 1/1999 | Voudouris |
| 5,908,293 A | 6/1999 | Voudouris |
| 5,913,680 A | 6/1999 | Voudouris |
| 6,168,428 B1 | 1/2001 | Voudouris |
| 6,257,883 B1 | 7/2001 | Voudouris |
| 6,302,688 B1 | 10/2001 | Jordan et al. |
| 6,368,105 B1 | 4/2002 | Voudouris |
| 6,554,612 B2 | 4/2003 | Georgakis et al. |
| 6,582,226 B2 | 6/2003 | Jordan et al. |
| 6,843,651 B2 | 1/2005 | Orikasa |
| 6,939,133 B2 | 9/2005 | Voudouris |
| 6,984,127 B2 | 1/2006 | Lai |
| 7,014,460 B2 | 3/2006 | Lai et al. |
| 7,063,531 B2 | 6/2006 | Maijer et al. |
| 7,186,114 B2 | 3/2007 | Navarro |
| 7,192,274 B2 | 3/2007 | Stadtmiller et al. |

(Continued)

*Primary Examiner* — Ralph Lewis
(74) *Attorney, Agent, or Firm* — McMillan LLP

(57) ABSTRACT

An orthodontic bracket that having a clip angulated toward the lingual direction in a diagonal orientation for active seating of archwires. The bracket having a lingual vertical slot, a pair of gingival tie wings and a pair of occlusal tie wings. An archwire slot extending mesiodistally across the body. A locking shutter with a pair of resilient arms connected by a guide bar and moveable between an open position allowing placement of the archwire and a closed position inhibiting removal of the archwire. A pair of tracks on each of the outer lateral surfaces of the body, extending from the occlusal tie wings and into the gingival tie wings. The tracks dimensioned to receive the resilient arms therein. The tracks extend in a substantially occlusal-gingival direction, angled lingually by an angle Θ with respect to a plane parallel to a vertical that is perpendicular to the occlusal plane.

26 Claims, 17 Drawing Sheets

(56) References Cited

U.S. PATENT DOCUMENTS

| | | |
|---|---|---|
| 7,214,057 B2 | 5/2007 | Voudouris |
| 7,442,039 B2 | 10/2008 | Opin et al. |
| 7,585,171 B2 | 9/2009 | Hagelganz et al. |
| 7,674,110 B2 | 3/2010 | Oda |
| 7,780,443 B2 | 8/2010 | Hagelganz et al. |
| 7,878,802 B2 | 2/2011 | Hagelganz et al. |
| 7,909,603 B2 | 3/2011 | Oda |
| 9,339,353 B2 * | 5/2016 | Voudouris .............. A61C 7/287 |
| 2006/0110699 A1 | 5/2006 | Forster |
| 2006/0228662 A1 | 10/2006 | Lokar |
| 2006/0228664 A1 | 10/2006 | Castner |
| 2006/0269895 A1 | 11/2006 | Voudouris |
| 2009/0170049 A1 | 7/2009 | Heiser |
| 2010/0311004 A1 | 12/2010 | Voudouris |
| 2011/0076633 A1 * | 3/2011 | Bryant .................. A61C 7/287 |
| | | 433/11 |
| 2013/0236847 A1 | 9/2013 | Shin |

* cited by examiner

ORTHODONTIC BRACKET WITH ANGLED, CURVED SHUTTER

RELATED APPLICATIONS

This application is a continuation-in-part of U.S. patent application Ser. No. 13/852,351 filed Mar. 28, 2013, which claims priority to U.S. Provisional Application No. 61/616,462 filed Mar. 28, 2012; the contents of all of which are herein expressly incorporated by reference.

FIELD OF THE INVENTION

The present invention relates to the field of orthodontic brackets, and more particularly to a self-ligating bracket having active archwire retention.

BACKGROUND OF THE INVENTION

Orthodontic treatment is effected by fixing small appliances often referred to as orthodontic brackets to a patient's teeth in an appropriate manner so as to correct malaligned teeth by applying an external force thereto through an archwire extending between the generally fixed orthodontic brackets. Directions mesial and distal mean generally left to right. Labial is the front surface, while lingual is defined as anything toward the direction of the tongue and it thereby stands to reason the word lingual is definitively and additionally defined as behind the labial surface. As to the structure of these orthodontic brackets, they are constructed of a body having a main archwire slot and other horizontally, vertically, diagonally oriented slots used to house a clip and are adhered directly on the labial or lingual sides of the teeth or welded to metal bands attached to the teeth by cementing or by some other method, as is generally known in the art.

As the form of use of the orthodontic bracket constructed as described above, a flexible archwire, which is curved so as to conform to a dental arch, is placed in an archwire slot in the bracket, and the tooth can be aligned over time by the restoring force of the generally flexible archwire so that the teeth become well aligned. With the orthodontic bracket, a force can be applied to the tooth in a desired direction to change the direction in which the tooth is aligned, rotated, tipped or torqued. This is effected by the three-dimensional inclination of the slot formed in the bracket body or by the desired bending of the archwire. Light, continuous forces are desirable for ideal biological movement that also reduce the risk of root resorption (root shortening).

Orthodontic treatment is accomplished by transmitting the restoring force of the archwires through brackets to the tooth roots. Generally, in an early period of the treatment, a thin, highly flexible round archwire is used, and an operation is required to loosen the ligature wire after ligating it such that the round wire freely slides within the slot (on a very low frictional basis). As treatment progresses, a thicker wire, a square or rectangular wire, and a more highly rigid wire eventually is used. When the alignment is nearly completed, the teeth are retained for a period of several months to prevent relapse. At this time, there are circumstances where the tooth is strongly fastened by a ligature wire so that it practically does not shift.

Various types and designs of self-ligating brackets are known in the art that provide different advantages, or solve particular problems that can also depend on the patient's oral physiology. One type of self-ligating bracket uses a slider mechanism, such as a flat cap or plate that slides in a linear direction within grooves or guides, to retain the archwire in the archwire slot. At one end of the slider mechanism's range, the archwire slot is closed and at the other, it is open. Any of a variety of structures can be used to bias or retain the slider mechanism in its open or its closed position. The invention provides an improvement to this type of passive self-ligating bracket.

One example of this type of bracket is shown in U.S. Pat. No. 6,168,428 to Dr. John Voudouris issued Jan. 2, 2001, and specifically at FIGS. 48 to 52. In this bracket, a spring member in the form of a resilient shim 720 located lingually to the labial face of the bracket, projects gingivally and has a jog directed lingually toward the archwire slot 3240d and presents a generally convex surface 722 towards the archwire slot 3240d. The gingival edge 724 of the shim 720 recurves gingivally after being directed lingually.

As the arms 3540 slide within the slots 3530 to move the clip 3538 to a closed position as shown in FIG. 49, the convex surface 722 of the shim 720 engages the archwire 3242d and provides a continuous biasing action against the archwire. As may be seen in FIG. 51, the resilience of the shim 720 allows the orthodontic bracket 3220d to accommodate different sizes and configurations of archwires 3242d while maintaining a continuous action against the archwire.

One of the problems associated with this passive, straight clip design is that the archwire is loose within the archwire slot and does not fully provide precise tooth positioning.

One modification of the Voudouris patent, to aid in the problem the passive clip resulting in looseness of the archwire in the slot mentioned above is addressed by United States Patent Publication No. 2011/0076633 published Mar. 31, 2011 to Bryant et al. This application provides for a slidable shim member (referred to therein as clip or shutter 20 shown in FIG. 1 of Bryant) slidable into two outer tracks extending in an occlusal-gingival direction on the outer lateral surfaces of the bracket, with a vertical trough extending in an occlusal-gingival direction between the outer tracks. The shim has two parallel outer arms and a central tongue between the outer arms. The outer tracks of the bracket slidably engage the outer arms of the clip and the central tongue is slidably engaged by the vertical trough of the bracket, thereby allowing the clip to slidably move between an open position in which the outer arms of the clip are retracted and a closed position in which the outer arms of the clip extend across the archwire slot to retain the archwire in the archwire slot.

One problem associated with the Bryant et al. disclosure is that the shim prevents movement of the archwire out of the archwire slot, but, depending on the size of the archwire being used, the shim generally is not in contact with the archwire and thus there is still movement or looseness of the archwire within the archwire slot, as is illustrated in FIG. 4 of this disclosure. This results in generally lower tooth rotation control and lower torque being applied to the archwire by the bracket overall as there is typically no contact between the shim and the archwire.

U.S. Pat. No. 7,621,743 to Orthodontic Research and Development discloses an orthodontic bracket including a mounting base for attachment to a tooth surface, an archwire slot formed on the base and sized for receiving an orthodontic archwire. A channel formed upon the base and transversely oriented to the archwire slot slideably retains a ligating slide member within the channel and closeable over the archwire slot for retaining the orthodontic archwire therein. The ligating slide member includes at least one coplanar resilient retention mechanism for exerting retention forces coplanar with the ligating slide member for holding the ligating slide member in a closed position. The orthodontic bracket has a bracket with a ligating slide member slideably retained within a dovetail shaped channel.

U.S. Pat. No. 8,414,292 to Lopes discloses a self ligating orthodontic bracket system includes a bracket, a slidable ligating member and at least one wedge locking ramp. The bracket includes an archwire slot defined therein, which is configured to receive an archwire. The ligating member slides along a slide path defined on the bracket and which extends transverse relative to the archwire slot. The wedge locking ramp is disposed on the slide path, wherein the wedge locking ramp is configured to deflect the ligating member vertically upward and away from an upper surface of the slide path, and over the wedge locking ramp when the ligating member travels along the slide path from an unlocked position to a locked position. The archwire is securely retained in the archwire slot when the ligating member is in the locked position, however, the archwire again is loose within the archwire slot in a passive system as shown in FIG. 4.

There is therefore a need in the art for a self-ligating orthodontic bracket having active seating of the archwire toward the base of the slot for more precise tooth alignment that addresses one or more of the aforementioned problems with the prior art.

SUMMARY OF THE INVENTION

The invention provides for a resilient locking shutter member slidable into two outer tracks angled lingually and extending in an occlusal-gingival direction on the outer lateral surfaces of the bracket, with a preferably angled occlusal-gingival opening between the two sets of occlusal-gingival tie wings forming a lingual vertical slot in relation to the labial surface of the bracket between the two sets of mesial and distal tie-wings and outer tracks, and that can be also angled in a lingual direction with respect to the vertical plane of the tooth. The resilient locking shutter member preferably has two parallel outer arms and a guide bar in relation to the labial surface of the bracket between the outer arms. The outer tracks of the bracket slidably engage the outer arms of the clip and the guide bar is slidably engaged by the occlusal-gingival opening with respect to the labial face of the bracket forming a lingual vertical slot of the bracket, thereby allowing the clip to slidably move between an open position in which the outer arms of the clip are retracted all the while preferably being maintained within the bracket body, for easy closing subsequently of locking shutter permitting positioning and removal of the archwire, and a closed position in which the outer arms of the clip extend across the archwire slot to retain the archwire in the archwire slot. The angling of the resilient locking shutter member within the angled outer tracks permits for contact between the resilient locking shutter member and an archwire in the archwire slot more often with round wires than passive systems for earlier rotation control and levelling. This contact occurs even more constantly with the progression to larger rectangular archwires to reach contact with the largest rectangular archwire at all times for greater torque control in the final, finishing stage. Furthermore, since the resilient locking shutter member is preferably made of a resilient nickel-titanium, chromium-cobalt, or spring steel material or alternatively any resilient material, it can contact the archwire directly and hold it toward the base of the slot by applying a lingual force along with a mild vertical vector. It should also be noted that resiliency is secondly, derived from shape design. The locking shutter has a U-shaped design that generates further resiliency. Thereby, the locking shutter made of resilient material, and with its specialized, open U-shape for additional resiliency as herein disclosed is able to flex uniquely labial-lingually and/or mesiodistally. With the above in mind, according to one embodiment of the invention, there is provided an orthodontic bracket having a body including a bonding base for attachment to the tooth, with respect to the labial face of the bracket a lingual vertical slot, a pair of laterally spaced gingival tie wings and a pair of laterally spaced occlusal tie wings, the gingival and occlusal tie wings projecting from a labial surface of the body; an archwire slot extending mesiodistally across the body and between the gingival and occlusal tie wings at opposed medial and distal sides of the body to accommodate an archwire; a locking shutter including at pair of resilient arm members and a connecting guide bar between the resilient arm members, the locking shutter moveable between an open position in which placement and removal of the archwire is facilitated and a closed position in which placement and removal of the archwire is inhibited; first and second tracks formed on each of first and second outer lateral surfaces of the body, extending from the gingival tie wings across the archwire slot and into the occlusal tie wings; the first and second tracks sized and otherwise dimensioned to receive the pair of resilient arm members therein; wherein the first and second tracks on the outer lateral surfaces extend in a substantially occlusal-gingival direction, angled lingually by an angle $\Theta$ with respect to a plane parallel to a vertical that is perpendicular to the occlusal plane such that the first and second tracks receive the resilient arm members therein.

According to an aspect of this embodiment, angle $\Theta$ is between 5 and 75 degrees in a lingual direction with respect to a plane approximately parallel with the surface of the tooth. The angle $\Theta$ may also be between 30 and 75 degrees, and preferably between 35 and 65 degrees.

According to another aspect of this embodiment, the first and second tracks start from the occlusal aspect of the bracket and extend approximately parallel to one another, and diagonally across the archwire slot at a distance labial to the base of the archwire slot so that an archwire can be secured in the archwire slot as the pair of resilient arms slide into the gingival wing tracks.

According to another aspect of this embodiment, the tracks start at a position closer to the labial surface portion of the occlusal tie wings and extend angularly in a lingual direction as the shutter moves gingivally such that end portions of the tracks are located in a more lingual portion of the occlusal tie wings and then similarly into the gingival tie wings to seat the archwire.

According to another aspect of this embodiment, the lingual guide bar further includes a depressed tongue portion extending towards the bonding base to snap-fit the resilient locking shutter for reduced rocking, into a locked position.

According to another aspect of this embodiment, the tracks further comprise depressions formed at gingival ends thereof; the locking shutter further comprises a protrusion formed on each of the arms; the depressions sized and otherwise dimensioned to receive the protrusions therein such that the protrusions compress into the depressions when the locking shutter is in the closed position.

An alternate embodiment includes the outer arms of the shutter having elbows that are curved outward or laterally in the mesial and distal directions for the elbows to lock into the depressions on the lateral aspect of the tracks in the occlusal and gingival wings.

According to another aspect of this embodiment, the archwire has one of a round cross-section where the locking shutter eventually rests more lingually, or a rectangular cross-section where the locking shutter is deflected more labially.

According to a second embodiment of the invention, there is provided an orthodontic bracket having a body including a bonding base for attachment to the tooth, a lingual vertical slot, a pair of laterally spaced gingival tie wings and a pair of laterally spaced occlusal tie wings, the gingival and occlusal tie wings projecting from a labial surface of the body; an archwire slot extending mesio-distally across the body and between the gingival and occlusal tie wings at opposed medial and distal sides of the body to accommodate an archwire; a locking shutter including at pair of resilient arm members and a lingual guide bar between the resilient arm members, the locking shutter moveable between an open position in which placement and removal of the archwire is facilitated and a closed position in which placement and removal of the archwire is inhibited; first and second tracks formed on each of first and second outer lateral surfaces of the body, extending from the occlusal tie wings across the archwire slot and into the gingival tie wings; the first and second tracks sized and otherwise dimensioned to receive the pair of resilient arm members therein; wherein the first and second tracks extend in a substantially occlusal-gingival direction, angled lingually by an angle $\Theta$ with respect to a plane parallel to a vertical that is perpendicular to the occlusal plane on the outer lateral surfaces such that the first and second tracks.

According to one aspect of this second embodiment, the first and second tracks start in the reverse direction, from a more labial position on the gingival aspect of the bracket and extend approximately parallel to one another, and diagonally across the archwire slot and into the latter aspects of the occlusal wings at a distance labial to the base of the archwire slot so that an archwire can be secured in the archwire slot as the pair of resilient arms slides in the tracks.

According to another aspect of this second embodiment, the centrally located guide bar starts parallel to the outer track arms then jogs in a approximately L-shaped pattern towards the lingual such that the gingival aspect of the guide bar end is located in a more lingual position than the outer track arms.

According to a third embodiment of the invention, an orthodontic bracket with a body has a bonding base for attachment to the tooth, a pair of laterally spaced gingival tie wings and a pair of laterally spaced occlusal tie wings. The gingival and occlusal tie wings project from a labial surface of the body. An archwire slot extends mesiodistally across the body and between the gingival and occlusal tie wings at opposed medial and distal sides of the body to accommodate an archwire. A locking shutter having two resilient arm members that are curved in a labial-lingual direction with a shutter protrusion that is also curved extending from each of resilient arm members and a centrally located and curved guide bar. The resilient arms and the lingual guide bar are curved in a convex shape relative to a base of the archwire slot, and the tracks are correspondingly curved to receive the curved resilient arms. The locking shutter is moveable between an open position in which placement and removal of said archwire is facilitated and a closed position in which placement and removal of said archwire is inhibited. Two tracks are formed on each of first and second inner lateral surfaces of the body and extends from said occlusal tie wings across said archwire slot and into said gingival tie wings. The tracks are sized and otherwise dimensioned to receive the two resilient arm members. A locking protrusion is formed on the occlusal tie wings and the shutter protrusion engages the locking protrusion when the locking shutter is placed in the closed position. Finally, the two tracks extend in a substantially occlusal-gingival direction, angled lingually by an angle $\Theta$ with respect to a vertical plane perpendicular with an occlusal plane of a tooth.

According to a fourth embodiment of the invention, the orthodontic bracket has a body with two inner tracks on the inner surfaces on the bracket body and extend in a substantially occlusal-gingival direction, angled gingivally and lingually with respect to a plane parallel with the vertical plane of a tooth on the inner lateral surfaces of the bracket body. The inner tracks begin in the occlusal tie wings and terminate in the gingival tie wings. The inner tracks start from the occlusal aspect of the bracket body and extend substantially parallel to one another, and diagonally to the archwire slot at a distance labial to the base of the archwire so that an archwire can be secured in the archwire slot as it slides in these inner tracks.

According to a fifth embodiment of the invention, the orthodontic bracket has a body including a bonding base for attachment to the tooth, a gingival tie wing and a pair of laterally spaced occlusal tie wings. The gingival and occlusal tie wings project from a labial surface of the body and at least one mating protrusion in the gingival wing extends occlusally toward said occlusal tie wings from the gingival wing to engage corresponding openings in the locking shutter. An archwire slot extends mesiodistally across the body and between the gingival and occlusal tie wings at opposed medial and distal sides of the body to accommodate an archwire. A locking shutter has at least one resilient retention element, mechanism, or fastener for engaging the mating protrusions. The locking shutter is moveable between an open position in which placement and removal of said archwire is facilitated and a closed position in which placement and removal of said archwire is inhibited. A track to receive the locking shutter is formed between the occlusal tie wings and extends directionally across the archwire slot. The track is sized and otherwise dimensioned to generally match the locking shutter. At least one relief groove is formed lengthwise along the edges of the track to facilitate a crimping of the at least one resilient mechanism, element, or fastener to lock around the mating protrusions in order to retain the locking shutter. Optionally, the occlusal tie wings may be crimped together to retain the locking shutter. The track extends in a substantially occlusal-gingival direction, angled lingually by an angle $\Theta$ with respect to a vertical plane perpendicular with an occlusal plane of a tooth.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only, and are not intended as a definition of the limits of the invention. In the accompanying drawings.

DETAILED DESCRIPTION

Figure 1A:
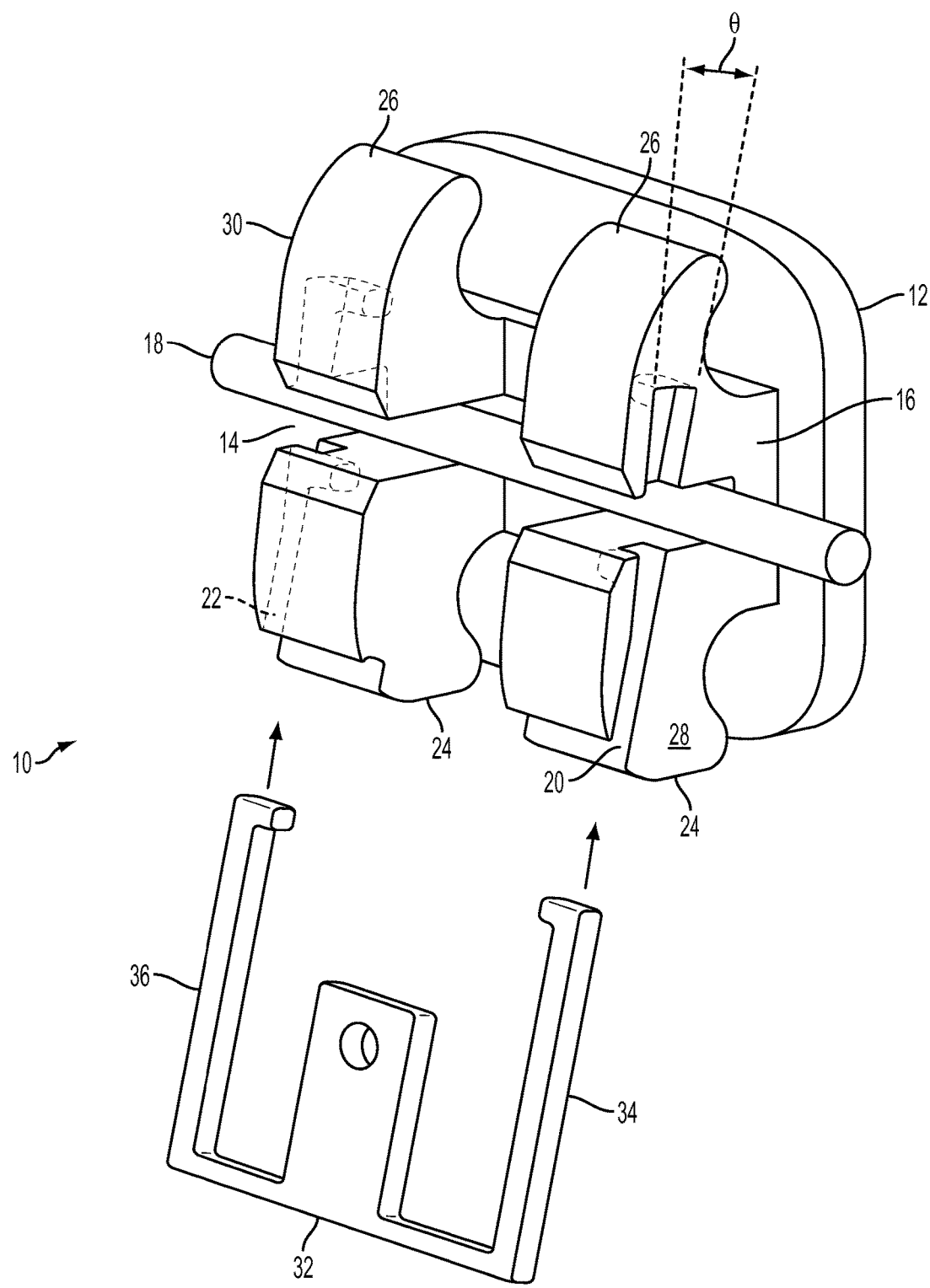
FIG. 1A is a perspective view of one embodiment of the invention, with the locking shutter prior to installation.
Figure 1B:
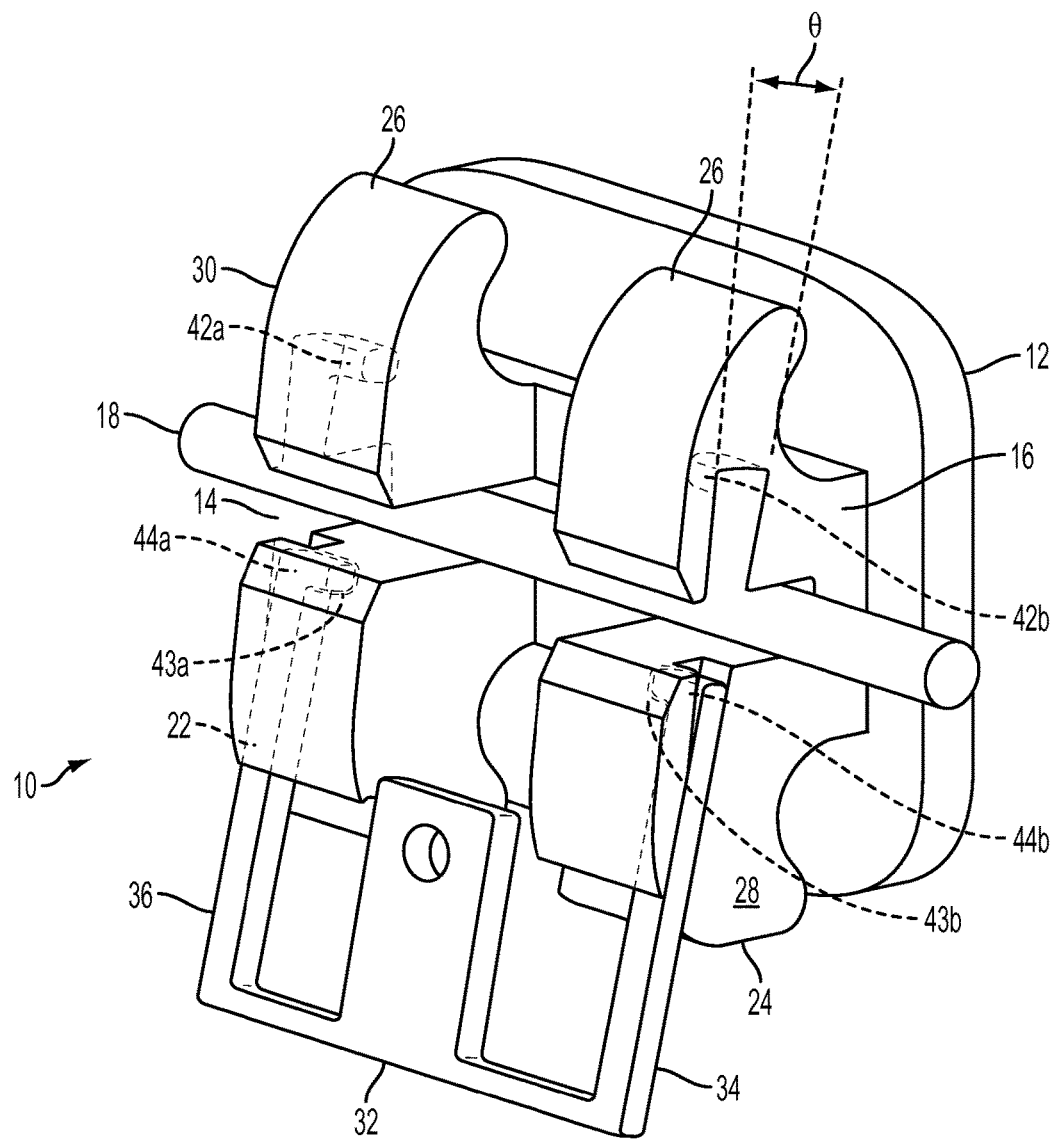
FIG. 1B is a perspective view of one embodiment of the invention, with the locking shutter locked into the bracket in the open position.
Figure 1C:
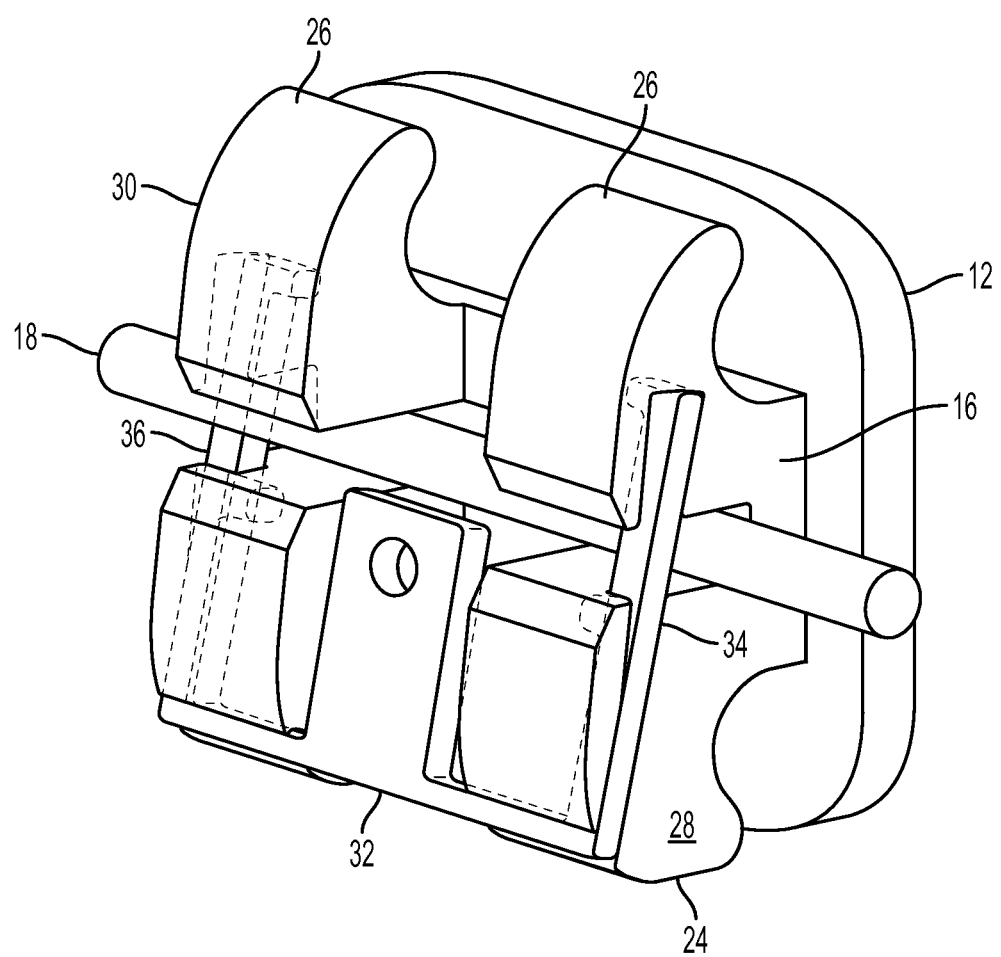
FIG. 1C is a perspective view of the embodiment of FIG. 1, with the locking shutter in the closed position.

Referring now to the FIGS. 1A to 1C, there is shown one embodiment of the self-ligating bracket according to the invention in which an orthodontic bracket 10 is provided having a bonding pad 12 for attachment to a tooth (not shown). An archwire slot 14 extends in a substantially mesiodistal direction across the body 16 of the bracket 10 with an open labial aspect to receive an archwire 18. Occlusal tie wings 24 and gingival tie wings 26 are provided on opposed sides of the body 16. These elements are not described in more detail as their purpose and functioning is generally known in the art.

Figure 2A:
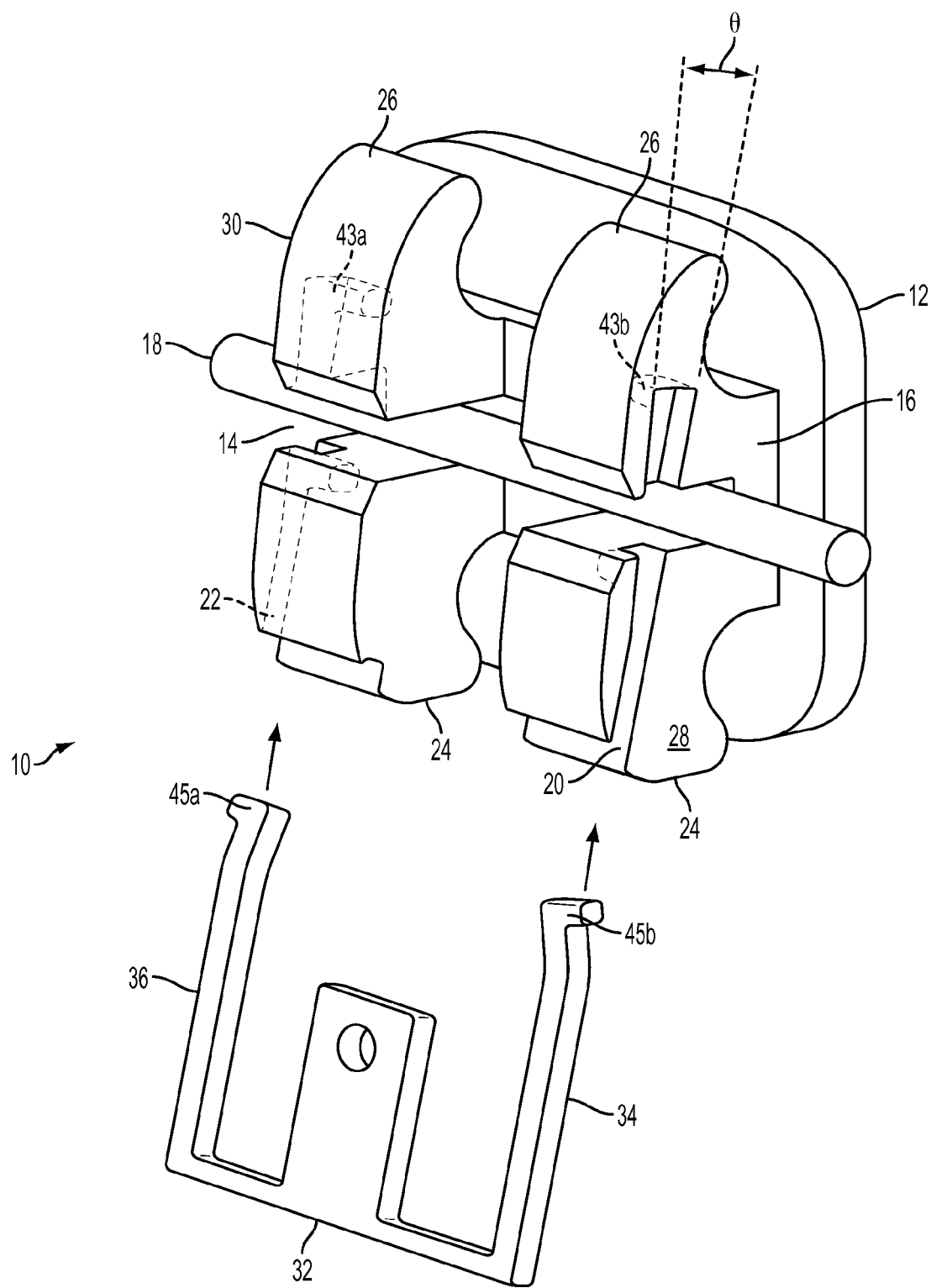
FIG. 2A is a perspective view of another embodiment of the invention, with an alternative locking shutter prior to installation.
Figure 2B:
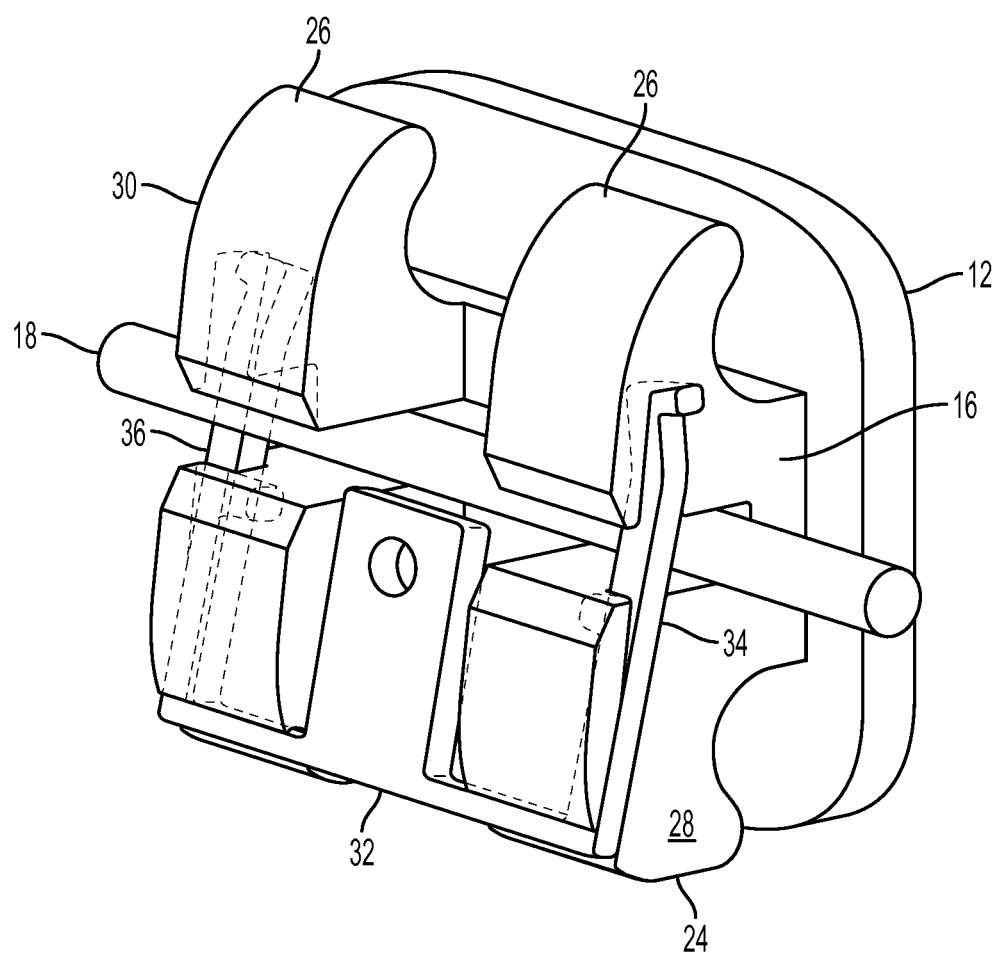
FIG. 2B is a perspective view of another embodiment of the invention, with the alternative locking shutter locked into the bracket in the closed position.
Figure 3:
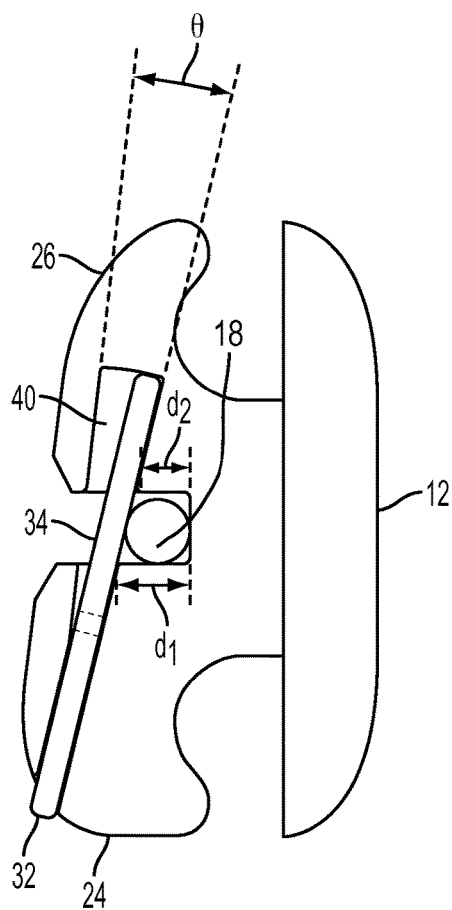
FIG. 3 is a side view of the embodiment of FIG. 1C.

In this embodiment of the invention, two outer tracks 20 and 22 extend in a substantially occlusal-gingival direction, angled gingivally by angle Θ (shown in FIGS. 1A to 2B, and more clearly in FIG. 3) with respect to a plane parallel with the vertical plane of a tooth on the outer lateral surfaces 28, 30 of the bracket 10. One outer track 20 runs along the mesial surface 28, and the other outer track 22 runs along the distal surface 30 of the bracket 10. Both outer tracks 20 and 22 start from the occlusal aspect of the bracket 10 and extend substantially parallel to one another, and diagonally across the archwire slot 14 at a distance labial to the base of the archwire 18 so that an archwire 18 can be secured in the archwire slot 14 as arms 34 and 36 of a locking shutter 32 slides in these outer tracks 20 and 22. These arms 34, 36 of the locking shutter 32 are connected by a horizontal component and the entire locking shutter 32 is preferably a resilient locking shutter, made of materials that are generally known in the art. The location of the outer tracks 20 and 22 preferably starts closer to the labial surface portion of the occlusal tie wings 24, and extends angularly in a gingival direction such that the end portions of the outer tracks 20 and 22 reside in a more lingual portion 40 of the gingival tie wings 26, as illustrated in FIG. 3. In this manner, the tracks 20 and 22 have little or no room for movement in the occlusal tie wings 24, and more room for movement in the gingival tie wings 26. This permits adaptation for different sized archwires 18 by permitting the ultimate angle of the locking shutter 32 to vary slightly.

This orientation of the outer tracks can also be reversed from those described above in the occlusal and gingival wings, where the resilient locking shutter 32 can open for instance upward toward the gingival tie wings. In addition, this can similarly occur in the lower brackets where the tracks start on the occlusal wings closer to lingual and angle toward the more labial surface in the gingival wings where the locking shutter opens downward toward the gingival wings. FIGS. 1C and 3 illustrate the locking shutter 32 of FIGS. 1A and 1B in the in-use or closed position, inserted into the tracks 20 and 22 (see FIG. 1), and applying an active force onto the archwire 18 in a direction towards the base of the archwire slot 14.

Figure 3B:
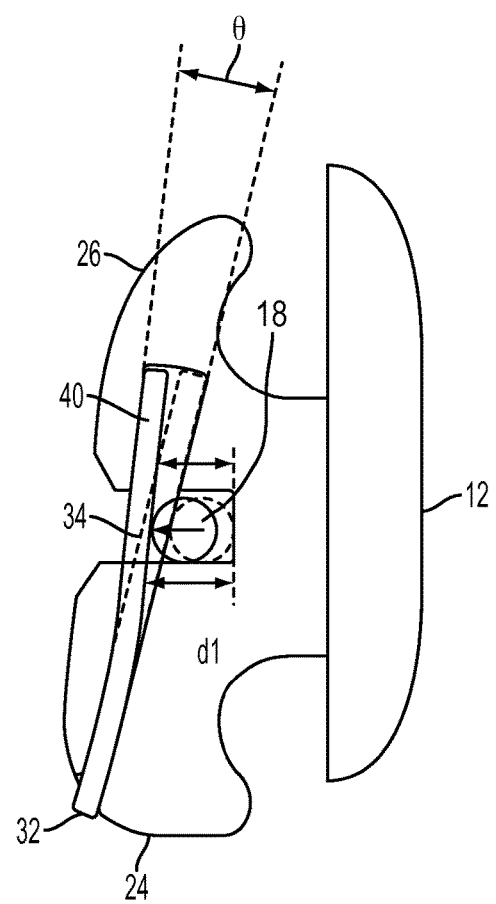
FIG. 3B is a side view demonstrating the cantilever effect during different stages of treatment.

FIG. 3B demonstrates a lingually displaced tooth initially wherein the archwire 18 pulls on the flexible clip labially where the shutter at the bottom engages the narrower tracks in the occlusal wings and creates the cantilever or "diving board" effect for the purpose of seating the flexible NiTi wire back into the base of the slot gradually with light, continuous force as indicated. The solid archwire 18 is the position early in the treatment and during the course of treatment the archwire 18 moves towards the more lingual position of the archiwire 18 shown in dotted outline.

The resilient locking shutter 32 is preferably formed from a resilient nickel-titanium, chromium-cobalt, titanium-molybdenum or spring steel material, or alternatively any resilient material that can apply a force to the archwire within the archwire slot as herein described.

Figure 4:
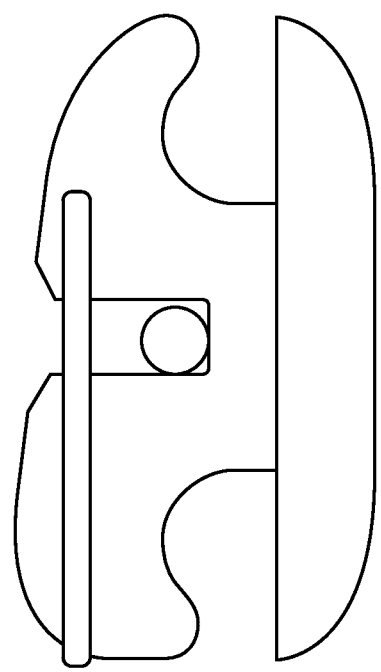
FIG. 4 is a side view of a prior art orthodontic bracket.
Figure 5A:
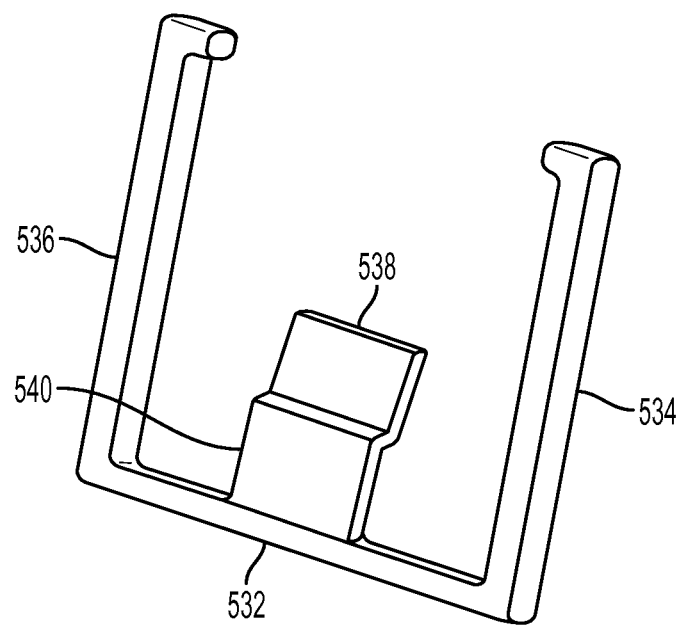
FIG. 5A is a perspective view of a locking shutter according to a second embodiment of the invention.
Figure 5B:
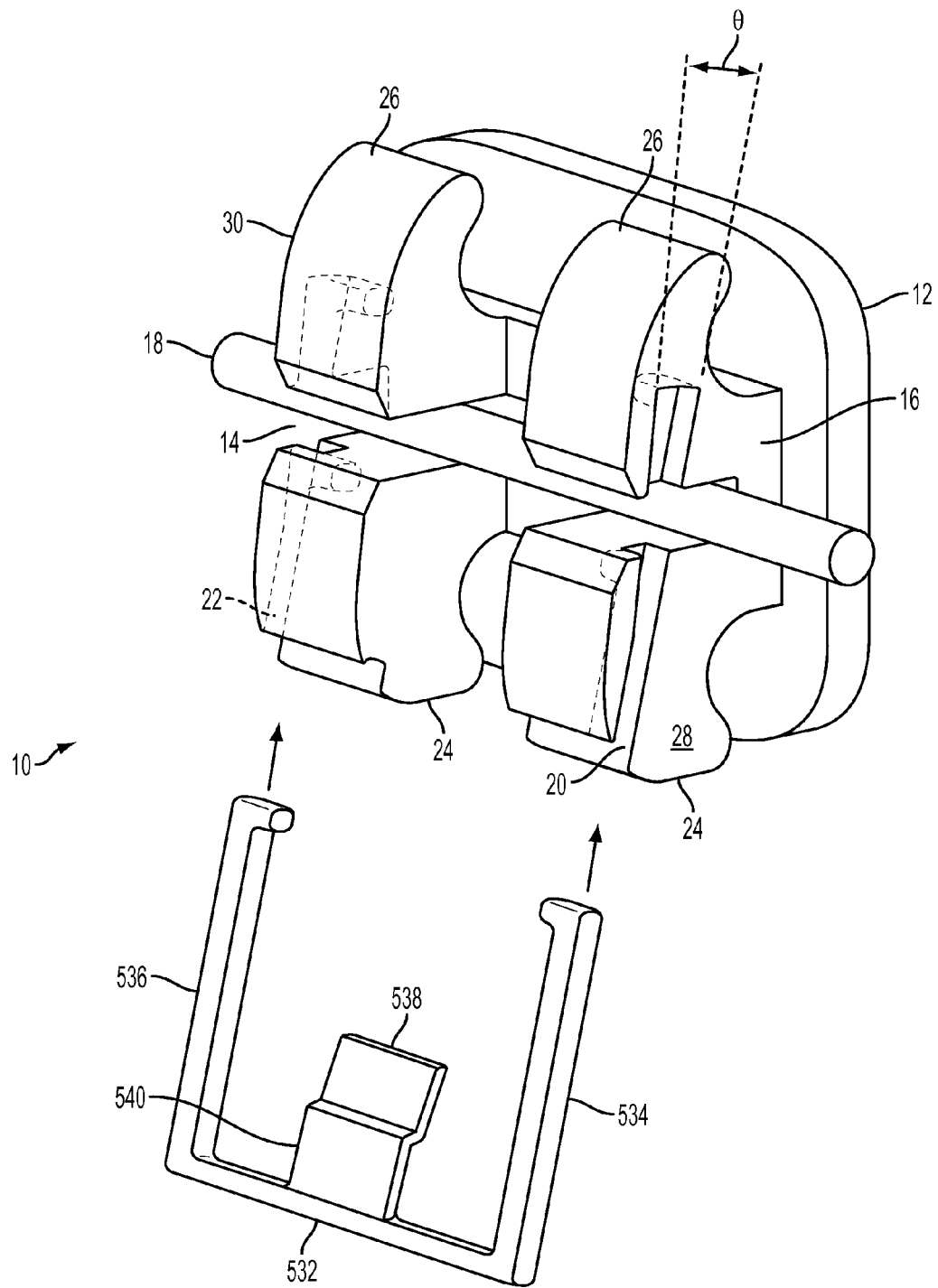
FIG. 5B is a perspective view of the second embodiment of the invention, prior to the locking shutter installation.
Figure 5C:
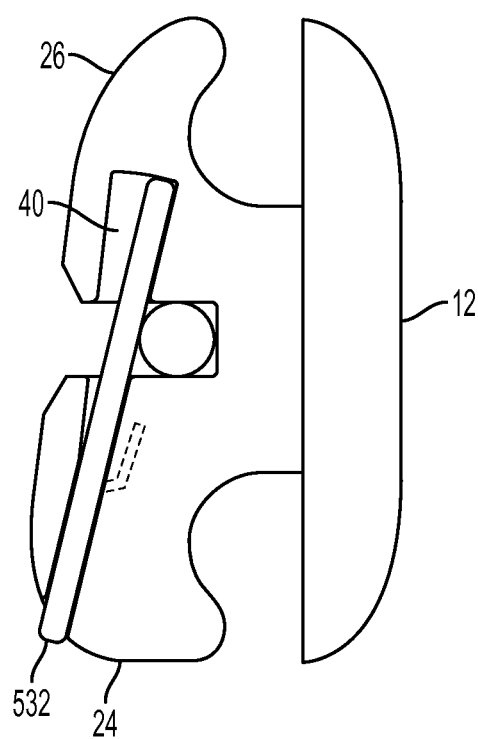
FIG. 5C is a side view of the embodiment of FIG. 5B, with the locking shutter in the closed position
Figure 5D:
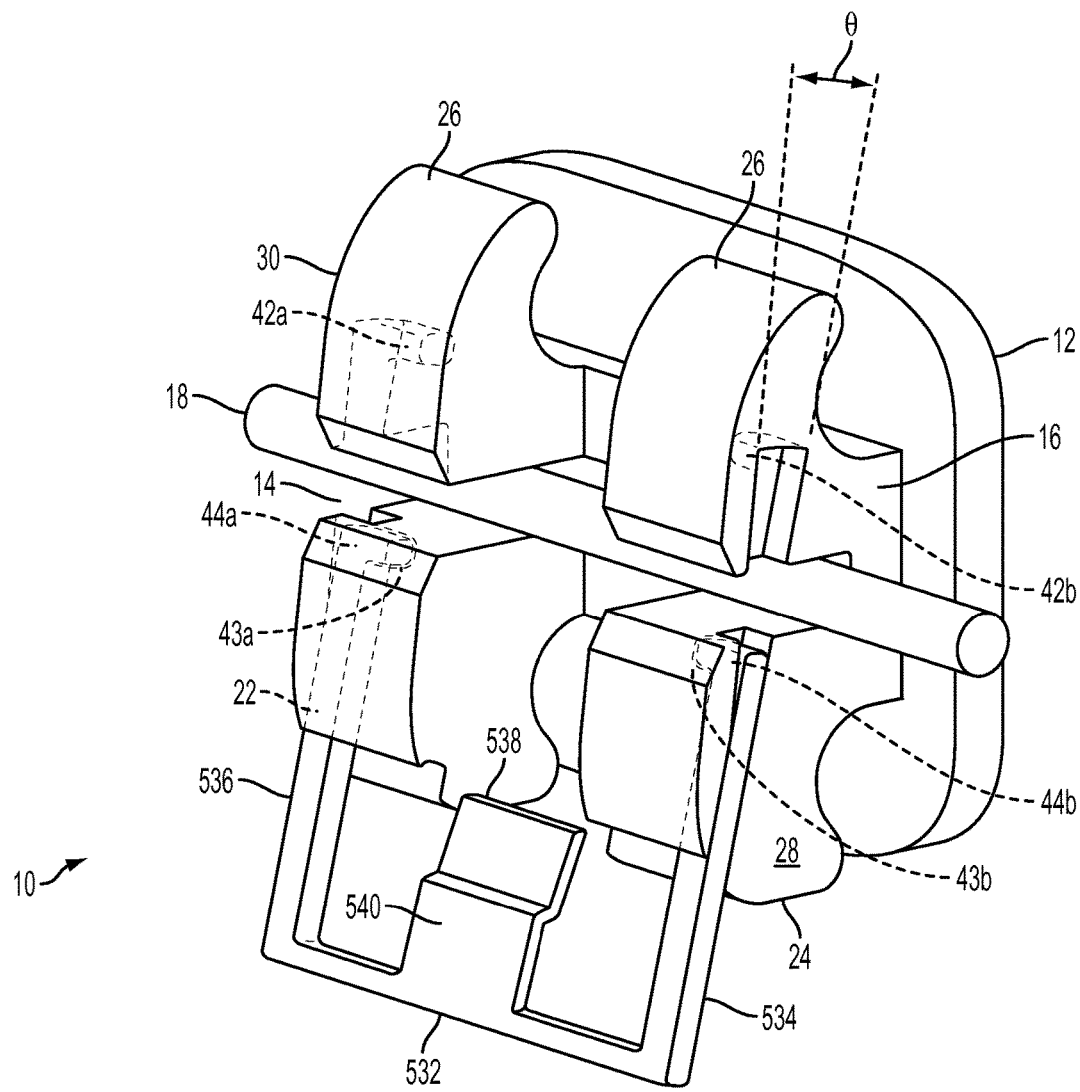
FIG. 5D is a perspective view of the second embodiment of the invention of FIG. 5B, with the locking shutter locked into the bracket in the open position.

Preferably, the distance from the more labial portion of the occlusal tie wings 24 where the outer tracks 20 and 22 begin, the specific angle at which the outer tracks 20 and 22 extend, and the distance from the more lingual portion of the gingival tie wings 26 where the outer tracks 20 and 22 may be determined based on the particular size of archwire 18 being used, the patient's oral physiology and other related factors. These distances and angles are determined such that an archwire in the archwire slot can be subjected to a force by the resilient locking shutter member. In some preferred examples, the angle Θ at which the outer tracks 20 and 22 extends is between 5 and 75 degrees in a lingual direction with respect to a plane parallel with a surface of the tooth, preferably, the angle is between 30 and 75 degrees, and more preferably between 35 and 65 degrees. In particular, the distance from the floor or base of the archwire slot 14 to a position where the outer tracks 20 and 22 cross the archwire slot 14 will be approximately the same as, or marginally less than the width or depth of a rectangular archwire 18. This distance is shown as d1 and d2 on alternate sides of the archwire slot 14 in FIG. 3. As will be appreciated by one skilled in the art, irrespective of the size, and in particular the cross-sectional width, of the archwire 18, the angled tracks 20, 22 of the invention enable the locking shutter 32 to actively apply a force onto the archwire 18, and therefore to maintain a prerequisite tension on the archwire 18 within the slot 14. In contrast, FIG. 4 shows a cross section of a prior art bracket and locking shutter, where the locking shutter extends generally in parallel with the base of the archwire slot. As can be seen, the archwire 18 is able to move around in the slot of FIG. 4, and little to no adaptability or compression by the passive shutter can be provided for archwires of different sizes.

Although each track 20 and 22 are shown herein with identical angles, the inventor contemplates that different angles may be used for each track dependent upon the patient's oral physiology, which tooth the bracket is adhered to, etc in order to further refine the active force placed on the archwire 18.

Returning to the present embodiment, the resilient locking shutter 32 is sized and otherwise dimensioned to slidably engage the outer tracks 20 and 22, and to extend angularly therethrough as illustrated. The resilient locking shutter 32 preferably includes outer arms 34 and 36 designed and adapted to correspond dimensionally with the outer tracks 20 and 22 such that the outer arms 34 and 36 may be slidably received in the outer tracks 20 and 22. Located at the gingival ends of the tracks 20 and 22 are small depressions 42*a* and 42*b*. Depressions 42*a* and 42*b* are used for locking the two flexible and small, dome-like, protrusions 44*a* (mesial) and 44*b* (distal) of the outer arms 34 and 36 when the resilient locking shutter closes. The outer arm protrusions 44*a* and 44*b* compress into the track depressions 42*a* and 42*b*. When the resilient locking shutter is in the open position within the bracket body, the outer arm protrusions 44*a* and 44*b* compress into the track depressions 43*a* and 43*b* located in the area nearest to the archwire slot of the occlusal tie-wing tracks. Another alternative is shown in FIGS. 2A and 2B where the outer arm protrusions are turned out mesially and distally forming elbows 45*a* and 45*b* that engages the track depressions 43*a* and 43*b*. Alternatively, the inventor contemplates that other retention or locking elements, fasteners, or mechanisms on the outer arms 34 and 36 may be used to retain the shutter 30 in the outer tracks 20 and 22.

Referring now to FIGS. 5A-5D, there is shown another embodiment of the invention in which a locking shutter 532 is provided having arm portions 534 and 536, respectively. In FIGS. 5A-5D, elements common with those of the embodiment of FIGS. 1-3 are correspondingly numbered, and reference is made to the description above for an identification of these elements. Those elements that differ are now discussed. Also preferably extending from the horizontal portion is lingual guide bar 538 that extends between the outer arms 534 and 536. The lingual guide bar 538 sized and otherwise dimensioned to slide into contact with the occlusal gingival opening or lingual vertical slot from the labial face of the bracket when the resilient locking shutter 532 is moved between the open and closed positions. The occlusal gingival opening or lingual vertical slot from the labial face of the bracket may serve as a guide to maintain proper alignment of the locking shutter with respect to the bracket 10 during assembly and movement of the resilient locking shutter 30. The lingual guide bar 538 helps to prevent the resilient locking shutter 30 from becoming wedged out of proper alignment with the outer tracks 20 and 22 which could otherwise result in damage to the resilient locking shutter. The occlusal gingival opening or lingual vertical slot from the labial face of the bracket is preferably wider and provides a degree of structural stability for the resilient locking shutter 30. Locking shutter 532 includes, in addition to arm portions 534 and 536, a depressed tongue portion 538 extending towards the bonding base 12 from the lingual guide bar 540 to snap-fit the resilient locking shutter 530 into a locked position.

When combined with the angled tracks 20 and 22, the locking shutter 532 having the depressed tongue portion permits a purchase step for an opening instrument while still maintaining the active application of force made possible by the invention herein described.

Figure 6A:
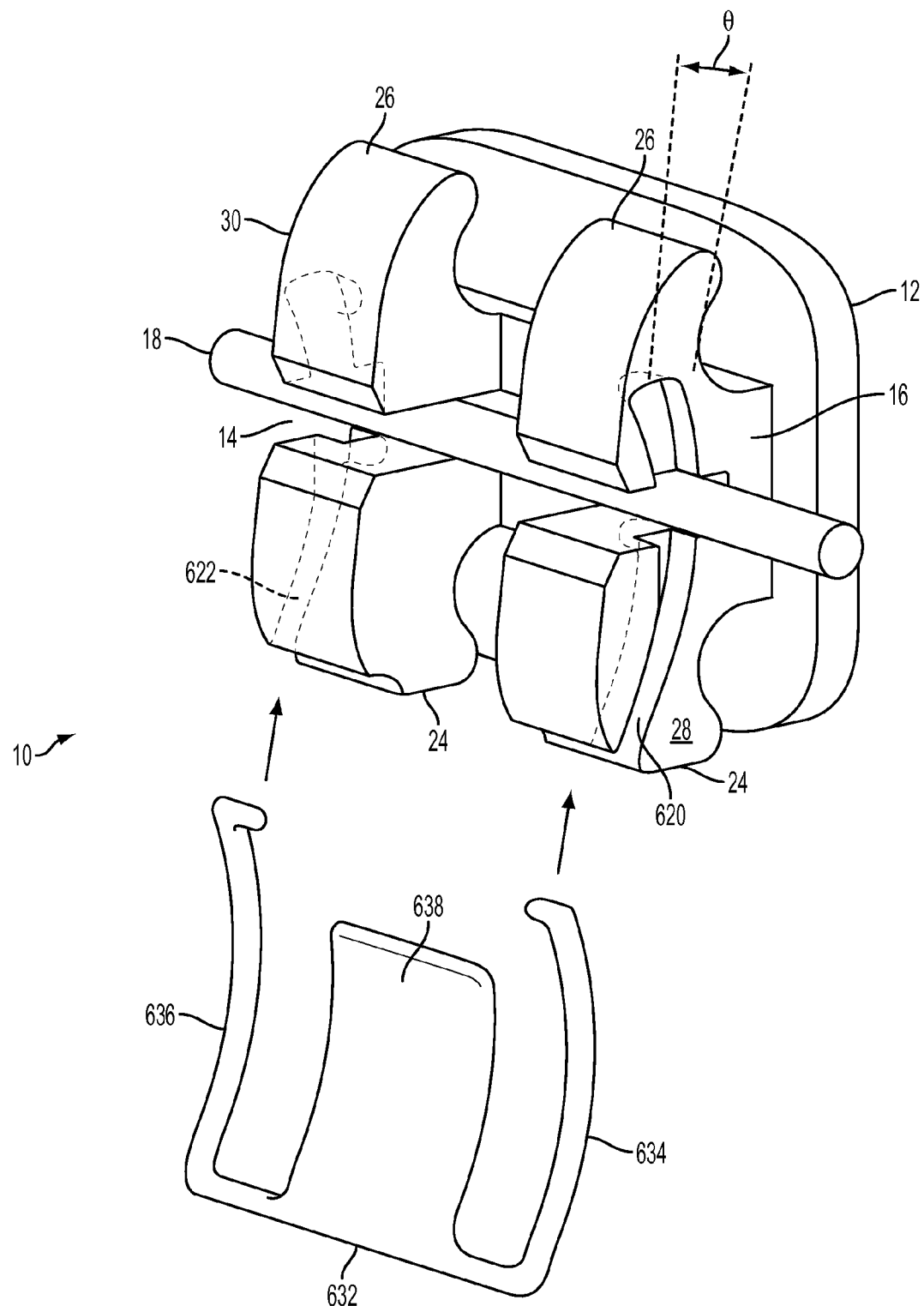
FIG. 6A is a perspective view of a third embodiment of the invention, with the curved locking shutter prior to installation.
Figure 6B:
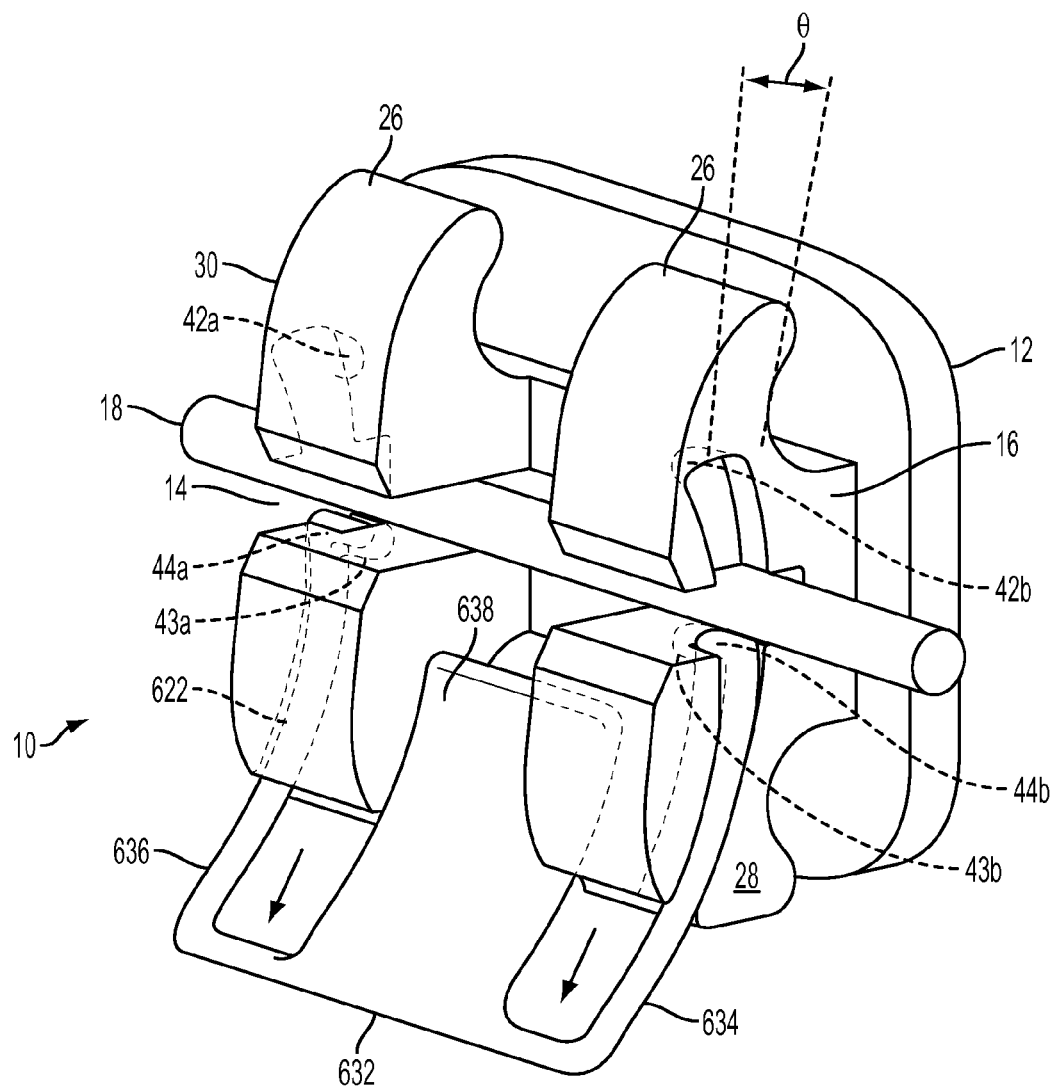
FIG. 6B is a perspective view of the third embodiment of the invention of FIG. 6, with the curved locking shutter locked into the bracket in the open position.
Figure 7:
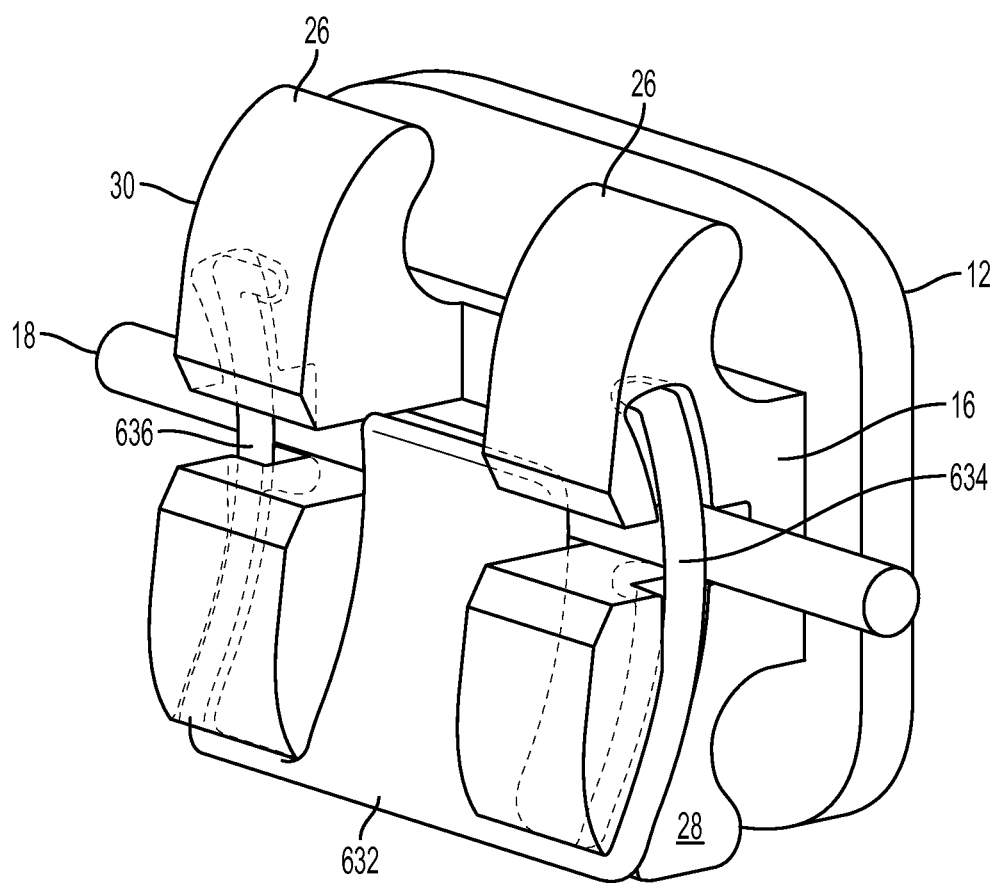
FIG. 7 is a perspective view of the embodiment of FIG. 6, with the locking shutter in the closed position.
Figure 8:
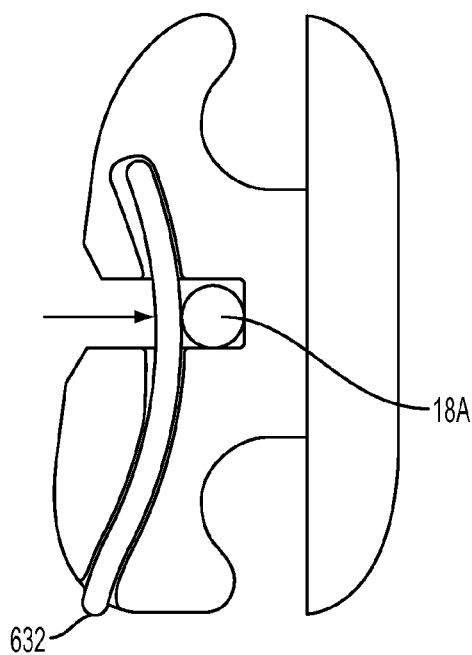
FIGS. 8 and 9 are side view of the embodiment of FIG. 7, with round and square archwires, respectively.
Figure 9:
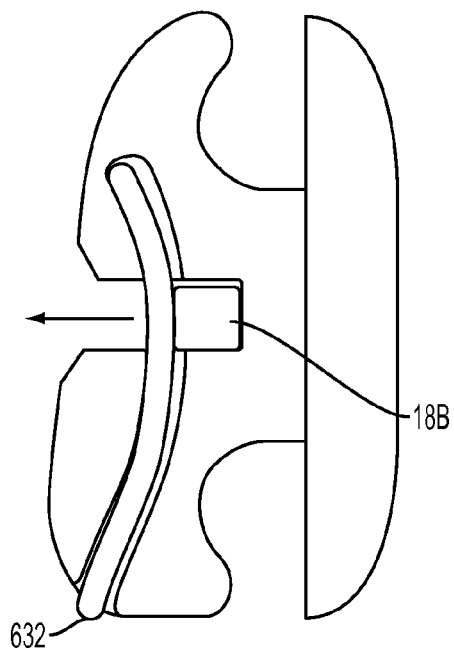

Referring now to FIGS. 6A and 6B and 7, there is shown yet another embodiment of the invention, in which the locking shutter 632, including the arms 634, 636 and the lingual guide bar 638 are mildly curved in convex to the base of the slot 14. To accommodate this, angled tracks 620 and 622 are correspondingly curved, in addition to being angled slightly as per the embodiment of FIG. 1A to 1C. The curved tracks 620, 622 of the bracket body, and curved arms 634, 636 of the resilient locking shutter allows seating of archwires of different cross-sectional shapes and sizes toward the base of the archwire slot. In particular, during orthodontic treatment, it is common that during the early stages of treatment, an archwire of rounded cross-section 18A, shown in FIG. 8, is used. During later stages of treatment, an archwire of square or rectangular cross-section 18B is used, as shown in FIG. 9. The curved locking shutter 632 enables contact of both round wires initially and larger rectangular wires during the finishing stages of orthodontic treatment, as illustrated in FIGS. 8 and 9. Furthermore, this embodiment permits tracks 620 and 622 to be sized correspondingly with the locking shutter 632 in both the occlusal and gingival tie wings. The ability to accommodate different sized archwires arises from the curvature in the locking shutter. With rectangular wires the curved outer arms will level mildly while still maintaining the angle position, as illustrated in FIG. 9. It is noted that the drawing in FIG. 9 is shown with deformations exaggerated for ease of understanding. An alternative embodiment provides that the gingival portions of tracts 620, 622 can also be made wider toward the labial, as in FIGS. 1A to 1C and FIGS. 5A-D, to permit the curved arms 634 and 636 to initially flex mildly in a labial direction with larger dimension archwires until the curved flexible arms seated the larger dimension archwire into the base of the slot.

As will now be apparent to a person skilled in the art, the angled positioning of the resilient locking shutters as herein described within the angled outer tracks results in an active self-ligating bracket that permits early and more constant contact between the resilient locking shutter (and therefore the bracket) and the archwire itself. Second, both the bracket tracks and the corresponding outer arms can additionally be curved toward the base of the slot so as to produce light, and continuous contact with both round wires initially and rectangular wires during finishing. Third, it should also be noted that the resilient locking shutter has a unique generally U-shape that makes it a more flexible design. This design or shaping for resiliency is additive to the actual resilient material used for overall greater flexibility. The locking shutter as herein disclosed is able to be highly flexible labial-lingually and/or mesiodistally. This can be observed by flexing the locking shutter easily between the fingers.

Furthermore, the design fourthly, in contrast to prior art brackets, shows a resilient locking shutter positioned largely outside or bilateral to the bracket body with an open U-shape design making it more resilient. These factors produce greater overall control of orthodontic tooth movement. The design also includes tracks on the outside of the bracket resulting in more flex permissible for the resilient locking shutter. Fifth, the design with a lateral, or outside-of-bracket position of the locking shutter as herein disclosed permits for a low profile bracket having a reduced thickness labial-lingually for patient comfort against the lips. This is enabled, at least in part, due to the active resilient forces applied to the archwire by the angled locking shutter/track combination which reduces the size of the bracket required to provide the requisite forces on the archwire. This active force system as herein disclosed produces light, continuous forces on the dentition for more physiological and biological tooth movement for potentially fewer iatrogenic complications potentially such as root resorption (shortening of the roots). The various problems identified in the prior art may thereby be obviated with use of the invention by distinctly improving rotation control, sliding control and torque control for finishing with a more active self-ligating bracket.

Figure 10A:
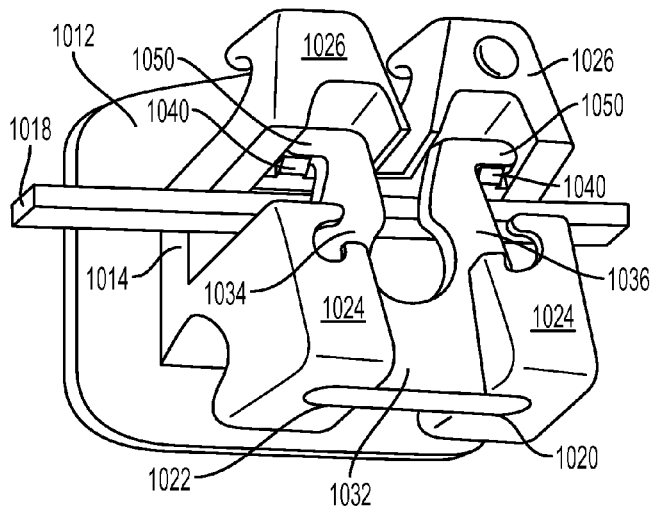
FIGS. 10A and 10B are a perspective view and a side view of the fourth embodiment of the invention, with the locking shutter in a closed position.
Figure 10B:
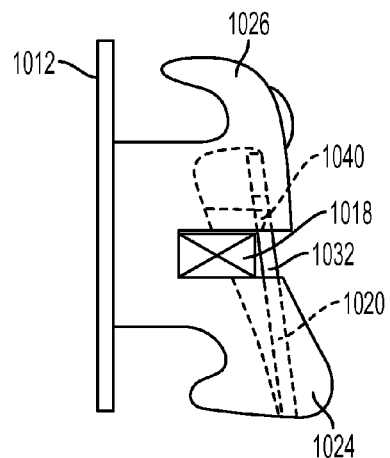

FIGS. 10A and 10B illustrate another embodiment of the bracket of the present invention. Two inner tracks 1020 and 1022 extend in a substantially occlusal-gingival direction, angled lingually with respect to a plane parallel with the vertical plane of a tooth on the inner lateral surfaces of the bracket body. The inner tracks 1020 and 1022 begin in the occlusal tie wings 1024 and terminate in the gingival tie wings 1026. The inner tracks 1020 and 1022 start from the occlusal aspect of the bracket body and extend into the gingival aspect, and are lingual to the labial face of the bracket body, and extend substantially parallel to one another, and diagonally to the archwire slot 1014 at a distance labial to the base of the archwire so that an archwire can be secured in the archwire slot 1014 as it slides in these inner tracks 1020 and 1022. The location of the inner tracks 1020 and 1022 preferably start closer to the labial surface portion of the occlusal tie wings 1024, and extend angularly in a gingival and lingual direction such that the end portions of the inner tracks 1020 and 1022 reside in a more lingual portion of the gingival tie wings 1026, as illustrated, with the portion of the tracks 1020 and 1022 on the gingival tie wings 1026 widening toward the top of the gingival tie wings 1026.

Alternatively, the orientation of the inner tracks 1020 and 1022 can be reversed from those described above in the occlusal 1024 and gingival wings 1026, where the resilient locking shutter 1032 can open for instance upward toward the gingival end. In addition, this can similarly occur in the other brackets where the tracks 1020 and 1022 start on the occlusal wings 1024 closer to lingual and angle toward the more labial surface in the gingival wings 1026 where the locking shutter 1032 opens downward toward the gingival.

The distance from the more labial portion of the occlusal tie wings 1024 where the inner tracks 1020 and 1022 begin, the specific angle at which the inner tracks 1020 and 1022 extend, and the distance from the more lingual portion of the gingival tie wings 1026 where the inner tracks 1020 and 1022 end is determined based on the particular size of archwire 1018 being used, the patient's oral physiology and other related factors. These distances and angles are determined such that an archwire 1018 in the archwire slot 1014 can be subjected to a force by the resilient locking shutter member 1032. In some examples, the angle at which the inner tracks 1020 and 1022 extends is between 5 and 75 degrees in a gingival direction with respect to a plane parallel with a surface of the tooth, preferably, the angle is between 30 and 75 degrees, and more preferably between 35 and 65 degrees.

Moreover, locking protrusions 1040 are provided on the occlusal tie wings 1024 on the left and right sides. The locking protrusions 1040 are preferably located adjacent the archwire slot 1014. Each locking protrusion 1040 has a sloped or ramped front surface.

A resilient locking shutter member 1032, sized and otherwise dimensioned to slidably engage the inner tracks 1020 and 1022 defined by distal and mesial walls of the occlusal tie wings 1024 and oriented transversely relative to the archwire slot 1014, and to extend angularly therethrough is also provided. The resilient locking shutter 1032 preferably includes arms 1034 and 1036 designed and adapted to correspond dimensionally with the inner tracks 1020 and 1022 such that the arms 1034 and 1036 may be slidably received in the inner tracks 1020 and 1022. Each of the inner arms 1034 and 1036 has a protrusion or ear portion 1050 located at the free gingival end thereof and extending away from the ear portion 1050 of the opposite arm 1034 (or 1036). The ear portion 1050 prevents the locking shutter 1032 from being displaced when in use by preventing the locking shutter 1032 from moving from the closed position to an open position accidentally. Each ear portion 1050 is configured to span approximately, mesiodistally, the entire archwire slot 1014 such that when the shutter 1032 is in the closed or locked state, a first edge of the ear portion 1050 engages a gingival surface of the corresponding locking protrusion 1040 and the archwire 1018 is retained in the archwire slot 1014. The resilient shutter 1032 slides along the inclined inner tracks 1020 and 1022.

Accordingly, when the shutter 1032 slides within the inclined inner tracks 1020 and 1022 from an open position toward a closed or locked position, the sloped or ramped front surface of the locking protrusion 1040 deflects the first edge of the corresponding ear portion 1050 vertically upward and away from, at an oblique angle relative to the inner tracks 1020 and 1022, over the locking protrusion 1040, and across the archwire slot 1014. Once the ear portions 1050 slide beyond the corresponding locking protrusion 1040, a portion of each ear portion 1050 rests on a part of the inner tracks 1020 and 1022 located on the gingival tie wing 1026 of the bracket body and are positioned lingually relative to the labial face of the bracket body, and a remaining portion of each ear portion 1050 spans the opening of the archwire slot 1014. The gingival portion of the locking protrusion 1040 is abutted by the first edge of each ear portion 1050 wherein the ear portions 1050 are locked behind the corresponding locking protrusion 1040 free of a transverse, coplanar or parallel locking force being exerted by the shutter 1032. The gingival portion of each locking protrusion 1040 prevents the corresponding ear portion 1050 from sliding toward the open position or the occlusal tie wings 1024.

Figure 11A:
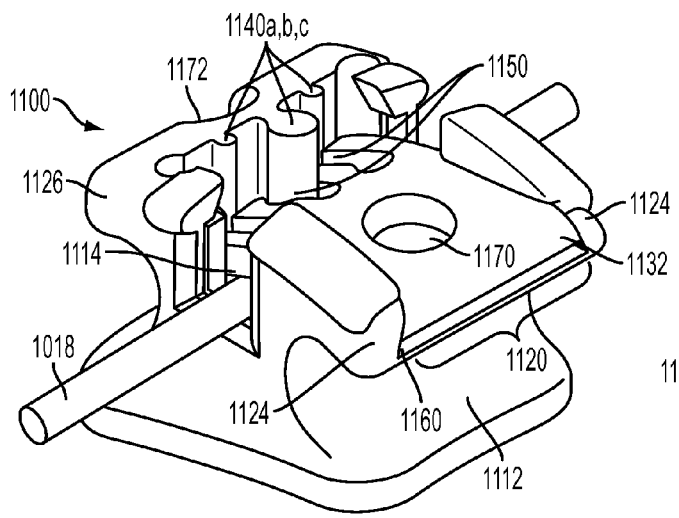
FIGS. 11A and 11B are a perspective view and a side view of the fifth embodiment of the invention, with the locking shutter in a closed position.
Figure 11B:
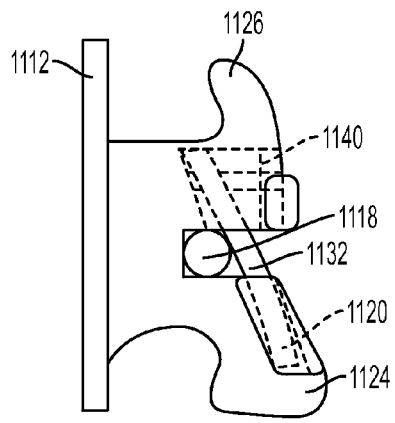

According to the fifth embodiment of the present invention, FIGS. 11A and 11B illustrates a self-ligating orthodontic bracket 1100 similar to the previous embodiments. The rounded bracket 1100 includes a bonding pad 1112 for attachment to a tooth surface, an archwire slot 1114 formed in the bracket body and sized for receiving an orthodontic archwire 1118, and a locking shutter 1132 for retaining an archwire within the archwire slot 1114. The locking shutter 1132 slides within an inner channel 1020 formed between sides of the occlusal wings 1024 and oriented transverse to the archwire slot 1114. The inner channel 1020 extends in a substantially occlusal-gingival direction, angled lingually with respect to a plane parallel with the vertical plane of a tooth on the inner lateral surfaces of the bracket body 1100. The shutter 1132 includes one or more resilient retention elements, fasteners, or mechanisms 1150 for holding the shutter 1132 in a closed position retaining the archwire 1118 within the archwire slot 1114.

The one or more resilient retention features 1150 may comprise portions of the shutter 1132 formed to allow coplanar deflection and subsequent engagement with one or more mating protrusions 1140. In the present embodiment, the resilient retention features 1150 are deflected outward, perpendicular to the inner track formed by sides 1120, for lockable engagement with a mating protrusion 1140*b* and smaller secondary protrusions 1140*a,c*. In this configuration, the resilient retention features 1150 deflect and engage with the mating protrusions 1140 transverse to and coplanar with the inner channel formed between sides 1120.

Relief grooves 1160 may be formed into inner channel 1120 to facilitate crimping or coining of the channel sides 1124 inward in order to retain the shutter 1132 within the channel 1120. The relief grooves 1160 are formed lengthwise along the edges of base of the channel 1120. The relief grooves 1160 may be slightly reduced in size after the coining operation to crimp the sides 1124 inward. One benefit of the relief groves is that they improve the dimensional quality of the dovetail shaped channel 1120 to provide additional clearance within which the shutter 1132 may slide within the channel 1120. Alternatively, the channel sides 1124 may overhang the channel 1120 in order to retain the shutter 1132.

The slope of the inner track 1120 causes the shutter 1132 to exert an increasingly greater force by the shutter 1132 onto the archwire 1118 as the size of the type of archwire increases. As can be further observed, the shutter 1132 angles deeper into the archwire slot 1114 than show in FIG. 10B because the round archwire 1118 is radially smaller than the square archwire 1018. Optionally, the shutter 1132 may further have protrusions (not shown) on the lingual side for further engaging the archwire 1118. The protrusions forcibly restrain the archwire 1118 when the shutter 1132 is in a closed position effectively locking the archwire 1118 within the archwire slot 1120 and therefore improving mesial-distal control.

Furthermore, active engagement of the archwire 1118 within the archwire slot 1114 also permits improved control of crown inclination particularly when a rectangular archwire in the archwire slot 1114 are used. Any labial pull-out or twists along the locked archwire 1118 may be transmitted to the bracket body 1100 through the lingual protrusions on the shutter 1132 as well as contacts between the lengthwise edges of the archwire 1118 and the archwire slot 1114.

The bracket body 1100 and/or the shutter 1132 may include orthodontic tool features 1170 and 1172 to improve installation of the shutter 1132 in the bracket body 1100. For example, the recess 1172 on the top area of the gingival wing 1126 and the recess 1170 on the shutter 1132 may allow orthodontic tools such as a scaler, an explorer, tweezers, or pliers during installation. By design of the present embodiment, a scaler or explorer may be used with the recess 1172 to open or close the shutter 1132. Pliers or other gripping tool may be used with the recesses 1170 and 1172 to close the shutter 1132.

Figures 10C, 10D:
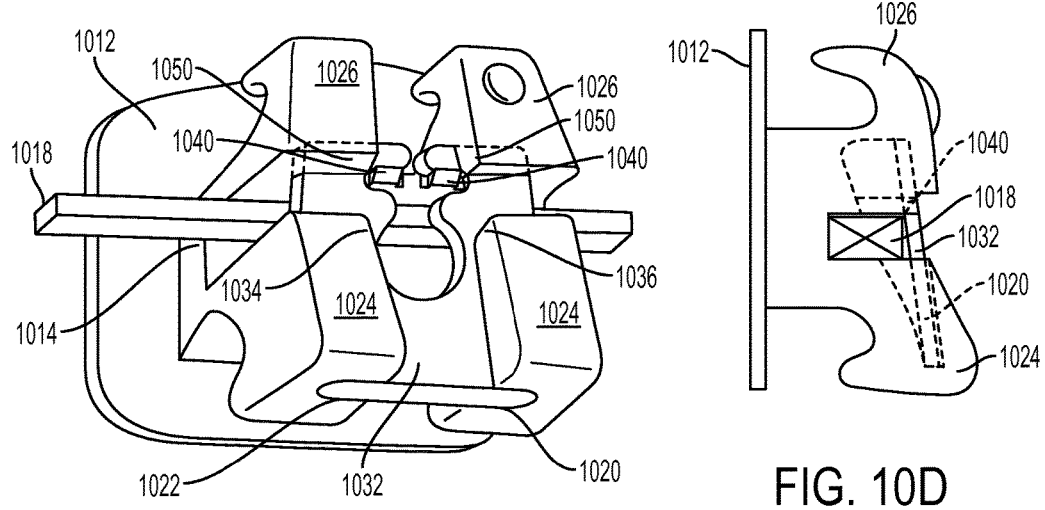
FIGS. 10C and 10D are a perspective view and a side view of an alternative embodiment of the invention demonstrating locking protrusions not on the gingival wings.

Although the embodiments described herein demonstrate protrusions, ear portions, or tabs extending in particular directions, the inventor contemplates that other configurations of these protrusions are possible to hold the shutter in a closed position. For example, the shutter protrusions or ear portions could extend inwardly towards the center of the bracket and engage one or more locking protrusions 1040 located within the lateral space between the gingival tie wings 1026 such as shown in FIGS. 10C and 10D. In this embodiment, the shutter 1032 is also wider providing additional mechanical advantage to rotate the tooth as the shutter becomes wider mesiodistally in the gingival area. Another example is the shutter protrusions could extend labially to engage one or more locking protrusions on the bracket that extend lingually. Another example is the protrusions could extend lingually and engage one or more locking protrusions on the bracket that extend labially. The inventor also contemplates other forms of locking elements, mechanisms, or fasteners known to those of skill in the art.

Figures 11C, 11D:
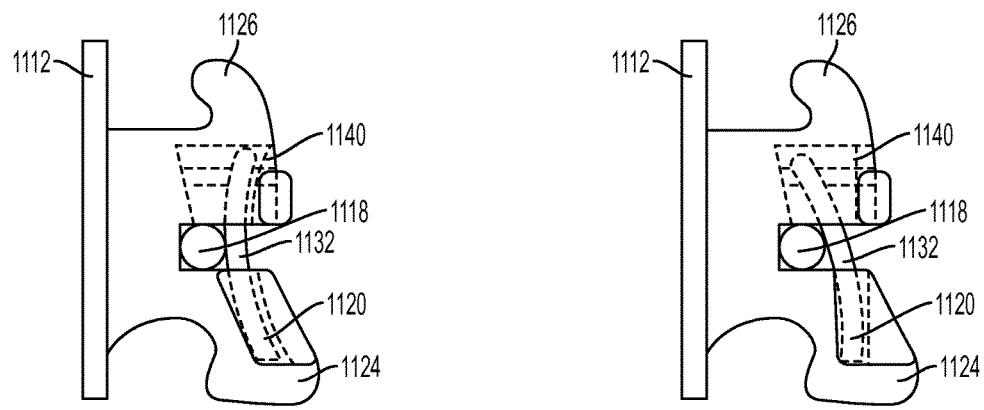
FIGS. 11C and 11D are a perspective view and a side view of an alternative embodiment of the invention demonstrating a convex and concave curvature of the shutter respectively.

Although some of the embodiments described herein show a straight or planar locking shutter 1032, the inventor contemplates that the shutter, with corresponding tracks or channels, could be curved in a convex, concave, or other curved form such as a sinusoid in order to achieve active retention of the archwire. One example of the convex or concave shutter 1132 embodiments are shown in FIGS. 11C and 11D. One advantage of a concave curve on the shutter 1132 is that it is more readily able to conform to a round archwire 1118 as can be seen in FIG. 11D. The curve preferably is shaped so a lingual force is exerted on the archwire yet allow the shutter to be opened and closed.

Although the embodiments described herein demonstrate a curved track generally corresponding to the curvature of the shutter, the inventor also contemplates that a curved shutter may be placed in a differently curved track or even a sufficiently sized straight track. The difference in curvatures between the track(s) and the shutter may provide additional active lingual force to hold the archwire within the slot. Furthermore, each track within a single bracket could have a different curvature from each other with some being concave, some being convex, some being straight, or any combination thereof.

Although some of the embodiments described herein show two arms on the shutter with two tracks, the inventor contemplates that the shutter could have more than two arms with corresponding numbers of tracks on the bracket.

Finally, it will be understood by one skilled in the art that the above-described embodiments are presented as examples only, with various modifications and alternatives permitted within the spirit and scope of the invention, (such as reversing the orientation of opening) which is not to be considered limited by the specific embodiments disclosed.

The invention claimed is:

1. An orthodontic bracket comprising:
    a body including a bonding base for attachment to a tooth, a pair of laterally spaced gingival tie wings and a pair of laterally spaced occlusal tie wings, said gingival and occlusal tie wings projecting from a labial surface of said body;
    an archwire slot extending mesiodistally across said body and between the gingival and occlusal tie wings at opposed mesial and distal sides of said body to accommodate an archwire;
    a locking shutter including first and second resilient arm members, a protrusion extending from each of said first and second resilient arm members, and a guide bar between said first and second resilient arm members, said locking shutter moveable between an open position in which placement and removal of said archwire is facilitated and a closed position in which placement and removal of said archwire is inhibited;

first and second tracks formed on each of first and second outer lateral surfaces of said body, extending from said gingival tie wings across said archwire slot and into said occlusal tie wings; said first and second tracks sized and otherwise dimensioned to receive said first and second resilient arm members therein;
each of said first and second tracks further including a pair of depressions sized and otherwise dimensioned to receive said protrusion therein;
one of said depressions located in an occlusal tie wing portion said respective track and the other of said depressions located in a gingival tie wing portion of said respective track;
wherein said first and second tracks extend in a substantially occlusal-gingival direction, angled lingually by an angle Θ with respect to a plane generally parallel to the labial face of the tooth, and said first and second tracks have a first thickness at a first end thereof in said occlusal tie wings and a second thickness at a second end thereof in said gingival tie wings; said first thickness being less than said second thickness such that said first and second tracks taper from said gingival tie wings to said occlusal tie wings.

2. The orthodontic bracket according to claim 1, wherein said taper provides for a cantilever effect of said locking shutter within said first and second tracks to accommodate different types of archwires.

3. The orthodontic bracket according to claim 2, wherein said archwire has one of a round cross-section where the locking shutter eventually rests more lingually or a rectangular cross-section where the locking shutter is deflected more labially.

4. The orthodontic bracket according to claim 1, wherein angle Θ is between 5 and 75 degrees.

5. The orthodontic bracket according to claim 1, wherein said guide bar further includes a depressed tongue portion extending towards the bonding base to guide the locking shutter into a locked position.

6. The orthodontic bracket according to claim 1, wherein said depressions are sized and otherwise dimensioned to receive said protrusions therein such that said protrusions compress into one of said depressions when said locking shutter is in said closed position; and wherein said protrusions compresses into the other of said depressions when said locking shutter is in said open position.

7. The orthodontic bracket according to claim 1, wherein said resilient arms are curved, and said tracks are correspondingly curved to receive said curved resilient arms therein.

8. The orthodontic bracket according to claim 7, wherein said resilient arms are convexly curved toward the base of said archwire slot, and said tracks are correspondingly curved to receive said curved resilient arms therein.

9. The orthodontic bracket according to claim 7, wherein said resilient arms are concavely curved, and said tracks are correspondingly curved to receive said curved resilient arms therein.

10. The orthodontic bracket according to claim 1, wherein said resilient arms are curved, and each of said tracks are straight and sized to receive said curved resilient arms therein.

11. The orthodontic bracket according to claim 1, wherein each of said resilient arms are straight, and said tracks are curved and sized to receive said straight resilient arms therein.

12. An orthodontic bracket comprising:
a body including a bonding base for attachment to the tooth, a pair of laterally spaced gingival tie wings and a pair of laterally spaced occlusal tie wings, said gingival and occlusal tie wings projecting from a labial surface of said body;
an archwire slot extending mesiodistally across said body and between the gingival and occlusal tie wings at opposed mesial and distal sides of said body to accommodate an archwire;
a locking shutter including first and second resilient arm members, a shutter protrusion extending from each of said first and second resilient arm members, said locking shutter moveable between an open position in which placement and removal of said archwire is facilitated and a closed position in which placement and removal of said archwire is inhibited;
first and second tracks formed on each of first and second outer side surfaces of said body, extending from said occlusal tie wings across said archwire slot and into said gingival tie wings; said first and second tracks sized and otherwise dimensioned to receive said first and second resilient arm members therein;
a locking protrusion formed gingival to said archwire slot, said shutter protrusion engaging said locking protrusion when the locking shutter is in the closed position;
wherein said first and second tracks extend in a substantially occlusal-gingival direction, angled lingually by an angle Θ with respect to a plane generally parallel to the labial face of a tooth, and said first and second tracks have first thickness at a first end thereof in said occlusal tie wings and a second thickness at a second end thereof in said gingival tie wings; said first thickness being less than said second thickness and said first and second tracks such that said first and second tracks taper from said occlusal tie wings to said gingival tie wings.

13. The orthodontic bracket according to claim 12, wherein said taper provides for a cantilever effect of said locking shutter within said first and second tracks to accommodate different types of archwires.

14. The orthodontic bracket according to claim 13, wherein said archwire has one of a round cross-section where the locking shutter eventually rests more lingually or a rectangular cross-section where the locking shutter is deflected more labially.

15. The orthodontic bracket according to claim 12, wherein angle Θ is between 5 and 75 degrees.

16. The orthodontic bracket according to claim 12, wherein said shutter protrusions are sized and otherwise dimensioned to oppose said locking protrusions when the shutter is placed in said closed position; and said first and second resilient arm members sufficiently flexible for said shutter and said locking protrusions to avoid each other when moving said shutter from said closed position to said open position.

17. The orthodontic bracket according to claim 16, wherein said locking protrusions are sloped towards said occlusal tie wings to facilitate installation of said shutter.

18. The orthodontic bracket according to claim 12, wherein said locking protrusion is formed on said gingival tie wings, said shutter protrusions engaging said locking protrusion when the locking shutter is placed in the closed position.

19. The orthodontic bracket according to claim 12, wherein said locking protrusion is formed in the space between said gingival tie wings, said shutter protrusion engaging said locking protrusion when the locking shutter is placed in the closed position.

20. The orthodontic bracket according to claim 12, wherein said locking protrusion is formed within said first and second tracks, said shutter protrusion engaging said locking protrusion when the locking shutter is placed in the closed position.

21. The orthodontic bracket according to claim 12, wherein said resilient arms are curved, and said tracks are correspondingly curved to receive said curved resilient arms therein.

22. The orthodontic bracket according to claim 21, wherein said resilient arms are convexly curved toward the base of said archwire slot, and said tracks are correspondingly curved to receive said curved resilient arms therein.

23. The orthodontic bracket according to claim 21, wherein said resilient arms are concavely curved, and said tracks are correspondingly curved to receive said curved resilient arms therein.

24. The orthodontic bracket according to claim 12, wherein said resilient arms are curved, and each of said tracks are straight and sized to receive said curved resilient arms therein.

25. The orthodontic bracket according to claim 12, wherein each of said resilient arms are straight, and said tracks are curved and sized to receive said straight resilient arms therein.

26. An orthodontic bracket comprising:
a body including a bonding base for attachment to the tooth, a pair of laterally spaced gingival tie wings and a pair of laterally spaced occlusal tie wings, said gingival and occlusal tie wings projecting from a labial surface of said body;
an archwire slot extending mesiodistally across said body and between the gingival and occlusal tie wings at opposed mesial and distal sides of said body to accommodate an archwire;
a locking shutter including first and second resilient arm members, a retaining element on each of said first and second resilient arm members, said locking shutter moveable between an open position in which placement and removal of said archwire is facilitated and a closed position in which placement and removal of said archwire is inhibited;
first and second tracks proximate to the first and second outer lateral surfaces of said body, extending from said gingival tie wings across said archwire slot and into said occlusal tie wings; said first and second tracks sized and otherwise dimensioned to receive said first and second resilient arm members therein;
each of said first and second tracks further including a retention element for engaging the retaining mechanism on each of said first and second arm members of said shutter;
wherein said first and second tracks extend in a substantially occlusal-gingival direction, angled lingually by an angle $\Theta$ with respect to generally a plane parallel to the labial face of a tooth;
and wherein said retaining element further comprises elbows that engage recesses in said retention element.

* * * * *